United States Patent [19]

Brieden et al.

[11] Patent Number: 5,856,485
[45] Date of Patent: Jan. 5, 1999

[54] PROCESS FOR PREPARING 2-PIPERAZINECARBOXYLIC ACID DERIVATIVES

[75] Inventors: Walter Brieden, Glis; Jean-Paul Roduit, Gröne, both of Switzerland

[73] Assignee: Lonza AG, Gampel/Valais, Switzerland

[21] Appl. No.: 722,149

[22] PCT Filed: Apr. 19, 1995

[86] PCT No.: PCT/EP95/01475

§ 371 Date: Dec. 23, 1996

§ 102(e) Date: Dec. 23, 1996

[87] PCT Pub. No.: WO95/29169

PCT Pub. Date: Nov. 2, 1995

[30] Foreign Application Priority Data

Apr. 20, 1994 [CH] Switzerland ............... 1205/94

[51] Int. Cl.$^6$ ............... C07D 498/04; C07D 241/04
[52] U.S. Cl. ............... 544/350; 544/388; 544/390
[58] Field of Search ............... 544/388, 390, 544/350

[56] References Cited

U.S. PATENT DOCUMENTS

| | | | |
|---|---|---|---|
| 4,766,125 | 8/1988 | Van Daele | 514/255 |
| 4,880,808 | 11/1989 | Van Daele et al. | 514/255 |
| 4,968,684 | 11/1990 | Van Daele et al. | 514/255 |
| 5,026,853 | 6/1991 | Van Daele et al. | 544/390 |
| 5,527,799 | 6/1996 | Vacca et al. | 514/252 |

FOREIGN PATENT DOCUMENTS

| | | |
|---|---|---|
| 0068544 | 1/1983 | European Pat. Off. |
| 0285219 | 10/1988 | European Pat. Off. |
| 0541168 | 5/1993 | European Pat. Off. |

OTHER PUBLICATIONS

Hosten et al, *Bull. Soc. Chim. Belg.* vol. 97, pp. 45–50, 1988.
*Houben–Weyl,* Methoden der. Org. Chemie. 4$^{th}$ Edition, vol. 15/1, (1974), Synthese von Peptiden, pp. 46 and 47.
*Tetrahedron Letters,* (1994), 35, 673–676, Askin et al.
*J. Org. Chem.,* (1985), 50, 1999–2003, Bailey et al.
*Indian J. Chem.,* vol. 13, No. 5, (1975), Part VII, pp. 468 to 472 (Sharma et al.).
*Indian J. Chem.,* vol. 16B, No. 11, (1978), Part XXXV, lines 1015 to 1018 (Khandelwal et al.).

Primary Examiner—Emily Bernhardt
Attorney, Agent, or Firm—Fisher, Christen & Sabol

[57] ABSTRACT

A process for preparing 2-piperazinecarboxamides in the form of their enantiomers or their enantiomer mixtures of the general formula:

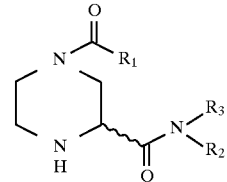

wherein $R_1$ is (a) unsubstituted or substituted alkyl or (b) —$OR_4$, wherein $R_4$ is unsubstituted or substituted alkyl, alkenyl or aryl, or (c) —$NR_5R_6$, wherein $R_5$ is hydrogen or alkyl and $R_6$ is alkyl, and $R_2$ and $R_3$ are identical or different and are hydrogen, unsubstituted or substituted alkyl, alkenyl or aryl, or the radical of an amino acid or an amino acid ester. A 2-piperazinecarboxylic acid of the formula:

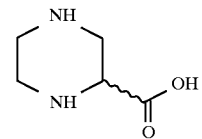

or a salt thereof, is first converted into an N-acyl derivative of the general formula:

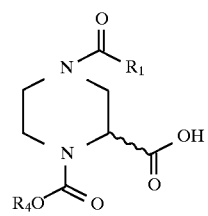

where $R_1$ and $R_4$ are as defined above. This compound is then cyclized in a second stage in the presence of a halogenating agent to form a piperazinecarboxylic anhydride of the general formula:

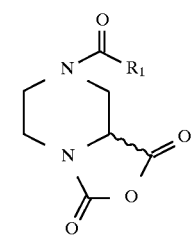

where $R_1$ is as defined above, which is finally reacted with an amine of the general formula:

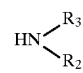

where $R_2$ and $R_3$ are as defined above, to give the end product of the general formula I. Certain piperazinecarboxylic anhydrides are also novel.

20 Claims, No Drawings

PROCESS FOR PREPARING 2-PIPERAZINECARBOXYLIC ACID DERIVATIVES

BACKGROUND OF THE INVENTION

1. Field of the Invention

The invention relates to a new process for preparing 2-piperazinecarboxamides of the general formula

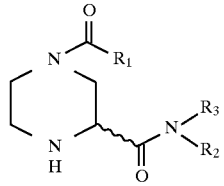

where $R_1$ is a) unsubstituted or substituted alkyl or b) —$OR_4$, where $R_4$ is unsubstituted or substituted alkyl, is alkenyl or aryl, or c) —$NR_5R_6$, where $R_5$ is hydrogen or alkyl and $R_6$ is alkyl, and $R_2$ and $R_3$ are identical or different and are hydrogen, unsubstituted or substituted alkyl, alkenyl or aryl, or the radical of an amino acid or an amino acid ester. The process of the invention enables both the (R) or (S) enantiomers of the 2-piperazinecarboxamides and the mixtures of the enantiomers, e.g., the racemates, to be obtained. The 2-piperazinecarboxamides are, inter alia, important intermediates for preparing orally active HIV-1 protease inhibitors European Published Patent Application No. A 541 168).

2. Background Art

In the previously known synthesis as described in European Published Patent Application No. A 541 168, the N-(t-butyl)-4-(t-butoxycarbonyl)-2(S)-piperazinecarboxamide of the formula

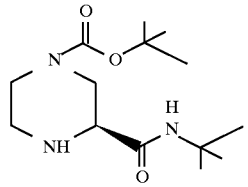

is prepared, according to Example 15, starting from the 2-(S)-piperazinecarboxylic acid by conversion into the 1-Z-protected and 4-BOC-protected 2-(S)-piperazine-carboxylic acid by formation of the tert-butylamide and finally by catalytic hydrogenation to remove the Z protective group. This synthesis is very complicated and is therefore only suitable for the laboratory scale. Furthermore, Tetrahedron Letters 1994, 35, 676, discloses the preparation of the compound of the formula Ia in an overall yield of 26% starting from 2-pyrazinecarboxylic acid by further conversion into the t-butylamide, hydrogenation to give the piperazinecarboxamide, racemate resolution using camphorsulphonic acid and finally by introduction of the BOC protective group. This synthesis too is not suitable for transfer to an industrial scale.

3. Broad Description of the Invention

There was therefore the object of developing a synthesis which allows the piperazinecarboxamides to be prepared simply, in good yields and on an industrial scale.

The object was able to be achieved by means of the process of the invention.

The first stage of this process comprises the conversion of a 2-piperazinecarboxylic acid of the formula

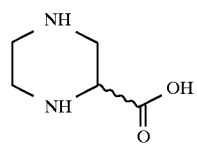

or a salt thereof into an N-acyl derivative of the general formula

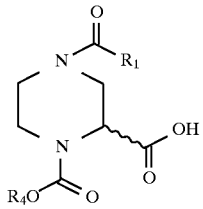

where $R_1$ and $R_4$ are as defined above.

DETAILED DESCRIPTION OF THE INVENTION

Alkyl is advantageously a straight-chain or branched, unsubstituted or substituted alkyl group having from 1 to 6 carbon atoms. Examples which may be mentioned of alkyl are methyl, ethyl, n- or i-propyl, n-, i- or t-butyl, pentyl and its isomers or hexyl and its isomers. Suitable alkenyl groups are vinyl, 1- or 2-propenyl (allyl), 1-, 2- or 3-butenyl, pentenyl and its isomers or hexenyl and its isomers. Aryl is advantageously an unsubstituted or substituted phenyl or naphthyl group. Substituents of the alkyl or alkenyl group which may be mentioned are, in particular, phenyl or halogens such as chlorine or bromine. A preferred representative of a substituted alkyl group is benzyl. Aryl substituents may be halogens such as chlorine or bromine or the specified alkyl groups. $R_1$ is preferably —$OR_4$, where $R_4$ is as defined above. $R_4$ is preferably benzyl, t-butyl or allyl.

The N-acylation to form the N-acyl derivatives of the general formula III can be carried out using acylation reagents known for blocking amino groups and under known conditions (see, for example, Houben-Weyl, Methoden der org. Chemie, 4th Edltion, Vol. 15/1, Synthese von Peptiden p. 46 ff).

For preparing the said preferred N-acyl derivatives, acylation reagents used are, for example, benzyl chloroformate for $R_4$=benzyl, di-t-butyl dicarbonate for $R_4$=t-butyl and, for example, allyl chloroformate for $R_4$=allyl.

In the cases where $R_1$ is not —$OR_4$, the acylation step can be preceded by the introduction, in accordance with the further meanings of $R_1$ and in a known manner, of an alkanoyl function such as acetyl or a carboxamide function on the nitrogen in the 4 position of the 2-piperazinecarboxylic acid.

The N-acylation proceeds virtually quantitatively. The resulting N-acyl derivative of the general formula III is advantageously cyclized, without being isolated, in the presence of a halogenating agent to form a piperazinecarboxylic anhydride of the general formula

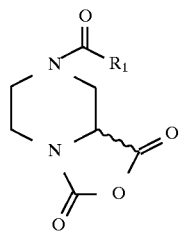

where $R_1$ is as defined above.

Appropriate halogenating agents are thionyl chloride, phosphorus halides such as phosphorus(V) chloride, phosgene or phosgene derivatives such as diphosgene and triphosgene. Preference is give to using thionyl chloride.

The cyclization is advantageously carried out in the presence of an N,N-disubstituted formamide in catalytic amounts of from 0.1 mol % to 30 mol %, based on the halogenating agent. Suitable N,N-disubstituted formamides are, for example, N,N-dibenzylformamide, N,N-diisopropylformamide, N,N-dimethylformamide or N,N-diethylformamide. Preference is given to using N,N-dimethylformamide.

The N,N-disubstituted formamides are used in excess, but can also additionally assume the function of the solvent it is of course also possible to use inert solvents such as tetrahydrofuran or acetonitrile.

To neutralize the hydrogen halide formed, it is advantageous to add a tertiary amine such as pyridine or triethylamine. The reaction temperature is advantageously in the range between 0° and 100° C.

Alternatively, as is described in J. Org. Chem. 1985, 50, 2200 ff., it is possible to convert the N-acyl derivative of the general formula III into a silyl ester by means of a halosilane and to cyclize this silyl ester using a halogenating agent to form the anhydride of the general formula IV.

However, preference is given to the first-mentioned variant.

The resulting piperazinecarboxylic anhydride of the general formula IV can be isolated from the reaction mixture after conventional work-up, advantageously by extraction using a suitable solvent. However, it is also possible to proceed directly with the subsequent stage without isolation of this intermediate.

The piperazinecarboxylic anhydride of the above formula IV is not known in the literature and, as an important intermediate in the synthesis of the invention, is likewise subject matter of the invention.

Preferred compounds of the general formula IV are the piperazinecarboxylic anhydrides having $R_1$=t-butyloxy, $R_1$=benzyloxy or $R_1$=allyloxy, in the form of its enantiomers or its enantiomer mixtures, e.g., the racemates. Particularly preferred compounds are t-butyl (R)-1,3-dioxotetrahydrooxazole[3,4-a]piperazine-7-carboxylate, t-butyl (S)-1,3-dioxotetrahydrooxazole[3,4-a]-piperazine-7-carboxylate, benzyl (R)-1,3-dioxotetrahydrooxazole[3,4-a]-piperazine-7-carboxylate, benzyl (R)-1,3-dioxotetrahydrooxazole[3,4-a]-piperazine-7-carboxylate, allyl (R)-1,3-dioxotetrahydrooxazole[3,4-a]-piperazine-7-carboxylate, and allyl (S)-1,3-dioxotetrahydrooxazole[3,4-a]-piperazine-7-carboxylate.

In the last stage of the process of the invention, the piperazinecarboxylic anhydride of the general formula IV is reacted with an amine of the general formula

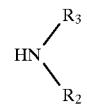

where $R_2$ and $R_3$ are as defined above, to give the end product of the general formula

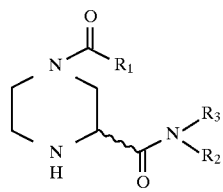

where $R_1$, $R_2$ and $R_3$ are as defined above.

Alkyl, alkenyl or aryl groups $R_2$ and $R_3$ advantageously have the detailed meanings given above. Preferably, $R_2$ is unsubstituted or substituted $(C_1-C_6)$-alkyl or $(C_2-C_6)$-alkenyl and $R_3$ is hydrogen. In particular, $R_2$ is t-butyl, allyl, benzyl or 1-phenyl-ethyl. 1-Phenylethyl can here be racemic or in the form of its 1-(S) or 1-(R) enantiomers.

Where $R_2$ or $R_3$ is a radical of an amino acid or an amino acid ester, these in principle encompass all radicals of amino acids which have the amino group in, for example, a terminal position or in the α or β position relative to the carboxyl group or to the ester group. For an overview, reference is made to chapter 11 of Houben Weyl, Methoden der org. Chemie, 4th Edition, Vol. 15/1, Synthese von Peptiden. Preferably, $R_2$ is the radical of one of the 20 essential L-α-amino acids, i.e., alanine, valine, leucine, isoleucine, proline, tryptophan, phenylalanine, methionine, glycine, serine, tyrosine, threonine, cysteine, asparagine, glutamine, aspartic acid, glutamic acid, lysine, arginine or histidine or their $(C_1-C_4)$ -alkyl esters and $R_3$ is hydrogen.

The reaction in the last stage advantageously proceeds in the presence of an inert solvent such as dichloromethane or aqueous alkaline solutions at a temperature in the range from −20° C. to the reflux temperature of the solvent. After a relatively short reaction time, the desired 2-piperazinecarboxamide of the general Formula I can be obtained in an overall yield of over 60%, based on the 2-piperazinecarboxylic acid used.

EXAMPLE 1 a1) Preparation of the 1,4-di(t-butyl) Ester of (S)-piperazine-1,2,4-tricarboxylic Acid 38.0 ml (273 mmol) of triethylamine were added to a slurry of 19.30 g (97.2 mmol) of 2-(S)-piperazine-carboxylic acid dihydrochloride (96%) in 100 ml of methanol and a solution Of 50.00 g (229 mmol) of di-tert-butyl dicarbonate in 100 ml of methanol was added dropwise over a period of 20 minutes. After stirring overnight at 50° C., the mixture was evaporated to dryness and the residue was admixed with 250 ml of water. The pH of the mixture was adjusted to 2 using 1N hydrochloric acid and the mixture was extracted four times with 150 ml of ethyl acetate. The combined organic extracts were dried over magnesium sulfate. The filtrate was evaporated to about 100 ml and admixed with 100 ml of n-hexane. The product was filtered off at 0° C., washed with a little n-hexane and dried. 27.90 g (92%) of the title compound were isolated as a white, crystalline solid.

$[\alpha]_D^{20}$=−176° (C=1; methanol)

M.p.=143.0°–144.5° C.

| $^1$H-NMR (CDCl$_3$, 400 MHz): δ | 10.70 (s, br, 1 H); |
| --- | --- |
| | 4.78–4.50 (m, 2 H); |
| | 4.10–3.72 (m, 2 H); |
| | 3.29–3.06 (m, 2 H); |
| | 2.94–2.78 (m, 1 H); |
| | 1.52–1.42 (m, 18 H). | a2) Preparation of the 1,4-di(t-butyl) ester of (R)-piperazine-1,2,4-tricarboxylic acid Starting from 2-(R)-piperazinecarboxylic acid dihydrochloride, the title compound was prepared in a yield of 92%.

$[a]_D^{20}$=+18.5° (C=1; methanol)

a3) Preparation of the 1,4-diallyl Ester of Piperazine-1,2,4-tricarboxylic Acid 10.20 g (73.80 mmol) of potassium carbonate were added to 5.00 g (24.6 mmol) of Z-(R,S)-piperazine-carboxylic acid dihydrochloride in 60 ml of acetone and 30 ml of water and the mixture was heated to 63° C. At this temperature, 9.50 g (78.8 mmol) of allyl chloroformate were added dropwise and the mixture was maintained at 63° C. for 2.5 hours. For the work-up, the mixture was, after cooling, admixed with 50 ml of water and the pH was adjusted to 2 using 6N hydrochloric acid, then the mixture was evaporated to dryness on a rotary evaporator. Extraction three times with 80 ml each time of ethyl acetate save 5.10 g (70%) of the pure title compound as a pale yellow oil.

| $^1$H-NMR (DMSO-d$_6$, 400 MHz): δ | 13.20–12.90 (m, 1 H); |
| --- | --- |
| | 6.00–5.83 (m, 2 H); |
| | 5.38–5.15 (m, 4 H); |
| | 4.64–4.48 (m, 5 H); |
| | 4.49–4.38 ("t", 1 H); |
| | 3.96–3.88 (m, 1 H); |
| | 3.88–3.78 (m, 1 H); |
| | 3.30–3.01 (m, 2 H); |
| | 3.00–2.88 (m, 1 H). |
| $^{13}$C-NMR (DMSO-d$_6$, 100 MHz): δ | 171.30 (s), |
| | 171.18 (s), |
| | 155.29 (s), |
| | 154.99 (s), |
| | 154.22 (s), |
| | 154.18 (s), |
| | 133.29–132.90 (d), |
| | 117.22–116.79 (t), |
| | 65.63–65.30 (t), |
| | 53.98 (d), |
| | 53.54 (d), |
| | 44.06 (t), |
| | 43.87 (t), |
| | 43.09 (t), |
| | 42.46 (t), |
| | 40.69 (t), |
| | 40.43 (t). | b1) Preparation of t-butyl (S)-1,3-dioxotetrahydrooxazole[3,4-a]-piperazine-7-carboxylate 3.60 g (45.5 mmol) of pyridine, 0.73 g (10 mmol) of N,N-dimethylformamide and 4.80 g (40.3 mmol) of thionyl chloride were added in succession to a suspension of 10.00 g (30.3 mmol) of the product from Example 1a1) in 50 ml of tetrahydrofuran. After stirring for 4 hours at 40° C., the mixture was worked up by addition of 300 ml of ethyl acetate and 150 ml of water. The aqueous phase was extracted twice more with 150 ml each time of ethyl acetate. The combined organic phases were dried over magnesium sulfate and evaporated. The residue was admixed with 20 ml of diethyl ether and cooled to 0° C. The product filtered off was washed twice with 10 ml each time of diethyl ether. After drying, 6.30 g (81%) of the title product was isolated as a white, crystalline solid.

$[\alpha]_D^{20}$=−24.2° (C=1; dichloromethane)

M.p.=116°–117° C. (decomposition)

| $^1$H-NMR (CDCl$_3$, 400 MHz): δ | 4.65–4.50 (s, br, 1 H); |
| --- | --- |
| | 4.23–4.19 ("dd", 2 H); |
| | 3.98 (dd, J = 3.4, |
| | 13.3 Hz, 1 H); |
| | 3.12 (dt, J = 3.9, |
| | 12.8 Hz, 1 H); |
| | 2.94–2.78 (m, 2 H); |
| | 1.49 (s, 9 H) | b2) Preparation of t-butyl (R)-1,3-dioxotetrahydro-[3,4-a]piperazine-7-carboxylate Starting from the 1,4-di(t-butyl) ester of (R)-piperazine-1,2,4-tricarboxylic acid, the title compound was prepared in a yield of 85%.

b3) Preparation of allyl 1,3-dioxotetrahydrooxazole piperazine-7-carboxylate.

1.07 g (9.00 mmol) of thionyl chloride were added to 1.80 g (6.03 mmol) of the 1,4-diallyl ester of piperazine-1,2,4-tricarboxylic acid in 20 ml of dichloromethane and the mixture was stirred at 30° C. for 2.5 hours. The solvent was then removed under reduced pressure. The $^{13}$C-NMR of the crude product shows the title compound and the 1,4-diallyl ester of piperazine-1,2,4-tricarboxylic acid.

The characteristic resonances of the carbonyl groups of the title compound are:

| $^{13}$C-NMR (DMSO-d$_6$, 100 MHZ): δ | 167.10 (s), |
| --- | --- |
| | 154.20 (s), |
| | 149.95 (s). | c1) Preparation of t-butyl (S)-3-(tert-butylcarbamoyl)-piperazine-1-carboxylate 2.56 g (10.0 mmol) of the product from Example 1b1) in 15 ml of dichloromethane were added drop-wise to a solution of 1.10 g (150 mmol) of t-butylamine in 15 ml of dichloromethane. After 45 minutes under reflux, the mixture was shaken three times with 10 ml each time of water and the organic phase was dried over magnesium sulfate. After removal of the solvent, the residue obtained was admixed with 20 ml of diethyl ether. After taking off the diethyl ether, 2.34 g (82%) of the title product were isolated as a crystalline solid.

$[\alpha]^{25}_{365\ nm}$=+102°–8° C. (C=1; methanol)

M.p.=105.0°–105.5° C.

| $^1$H-NMR (CDCl$_3$, 400 MHz): δ | 6.75–6.45 (s, br, 1 H); |
| --- | --- |
| | 4.13–4.02 (m, 1 H); |
| | 3.90–3.70 (s, br, 1 H); |
| | 3.20 (dd, J = 3.7, |
| | 9.3 Hz, 1 H); |

| |
|---|
| 3.05–2.80 (m, 3 H); |
| 2.80–2.70 (m, 1 H); |
| 2.05–1.90 (s, br, 1H); |
| 1.47 (s, 9 H); |
| 1.35 (s, 9 H). | c2) Preparation of t-butyl (R)-3-(tert-butylcarbamoyl)-piperazine-1-carboxylate Starting from t-butyl (R)-1,3-dioxotetrahydrooxazole[3,4-a]piperazine-7-carboxylate, the title was prepared in a yield of 70%.

$[\alpha]^{20} = -98.40°$ (C=1; methanol)

M.p.=103.5°–105.0° C.

EXAMPLE 2

Preparation of t-butyl 3(S)-[1(S)-phenylethylcarbamoyl]-piperazine-1-carboxylate and t-butyl 3(R)-[1-(S)-phenylethylcarbamoyl]piperazine-1-carboxylate 3.25 g (20.3 mmol) of t-butyl (R,S)-1,3-dioxotetrahydrooxazole[3,4-a]piperazine-7-carboxylate were added in portions to 5.20 g (42.9 mmol) of (S)-1-phenylethylamine in 50 ml of dichloromethane. After 1 hour at 40°–50° C., the mixture was shaken with water and 0.1N hydrochloric acid. After drying over magnesium sulfate, the solution was evaporated on a rotary evaporator and the two diastereomers were separated by means of MPLC (EtOAc/MeOH=5:1) and isolated as colorless oils.

t-Butyl 3(R)-[1(S)-phenylethylcarbamoyl]piperazine-1-carboxylate $R_f$=0.74 (EtOAc/MeOH=5:1)

| | |
|---|---|
| $^1$H-NMR (CDCl$_3$, 400 MHz): δ | 7.35–7.21 (m, 5 H), |
| | 7.20–7.12 (m, 1 H), |
| | 5.15–5.06 ("quint", 1 H), |
| | 4.08–4.01 ("dd", 1 H), |
| | 3.85–3.65 (m, 1 H), |
| | 3.31–3.25 ("dd", 1 H), |
| | 3.06–2.82 (m, 3 H), |
| | 2.76–2.67 ("t", 1 H), |
| | 2.04–1.90 (m, 1 H), |
| | 1.48 (d, J = 7.7 Hz, 3 H), |
| | 1.44 (s, 9 H). |
| $^{13}$C-NMR (CDCl$_{3, 100 MHz}$): δ | 169.92 (s), |
| | 154.42 (s), |
| | 142.96 (s), |
| | 128.45 (d), |
| | 127.08 (d), |
| | 125.83 (d), |
| | 79.80 (s), |
| | 58.02 (d), |
| | 48.13 (d), |
| | 46.2 (br, t), |
| | 43.86 (t), |
| | 43.4 (br, t), |
| | 28.15 (q), |
| | 21.74 (q). | t-Butyl 3(S)-[1(S)-phenylethylcarbamoyl]piperazine-1-carboxylate $R_f$=0.56 (EtOAc/MeOE=5:1)

| | |
|---|---|
| $^1$H-NMR (CDCl$_3$, 400 MHz): δ | 7.35–7.25 (m, 4 H), |
| | 7.25–7.17 (m, 2 H), |
| | 5.13–5.04 ("quint", 1 H), |
| | 4.08–4.00 ("dd", 1 H) |
| | 3.80–3.67 (m, 1 H), |
| | 3.29–3.23 ("dd", 1 H), |
| | 3.04–2.81 (m, 3 H), |
| | 2.73–2.63 ("t", 1 H), |
| | 2.04–1.90 (m, 1 H), |
| | 1.46 (d, J = 7.7 Hz, 3 H), |
| | 1.44 (s, 9 H). |
| $^{13}$C-NMR (CDCl$_3$, 100 MHz): δ | 169.88 (s), |
| | 154.33 (s), |
| | 142.92 (s), |
| | 128.31 (d), |
| | 126.97 (d), |
| | 125.80 (d), |
| | 79.68 (s), |
| | 57.90 (d), |
| | 48.09 (d), |
| | 47.0 (br, t), |
| | 43.72 (t), |
| | 43.5 (br, t), |
| | 28.06 (q), |
| | 21.63 (q). |

EXAMPLE 3

Preparation of t-butyl 3(S)-[1(S)-methoxycarbonyl-2-methylpropylcarbamoyl]piperazine-1-carboxylate 0.44 g (4.35 mmol) of triethylaminie was added dropwise- while- starring to 0.50 g (1.95 mmol) of t-butyl (S)-1,3-dioxotetrahydrooxazole[3,4-a]piperazine-7-carboxylate, and 0.67 g (4.00 mmol) of L-valine methyl ester hydrochloride in 20 ml of dichloromethane. After 15 minutes under reflux, the mixture- was cooled to room temperature, the pH was adjusted to 2 using 1N hydrochloric acid and the mixture was extracted with 40 ml of ethyl acetate. The aqueous phase was extracted twice more with 30 ml each time of ethyl acetate and the combined organic phases were dried over magnesium sulphate. The crude product (0.63 g, 94%) was purified by chromatography for complete characterization (silica gel, EtOAc/MeOE=5:1, $R_f$=0.58) and 0.24 g of the pure title compound was isolated as a colourless oil.

| | |
|---|---|
| $^1$H-NMR (CDCl$_3$, 400 MHz): δ | 7.38–7.25 (m, 1 H), |
| | 4.54–4.50 ("dd", 1 H), |
| | 4.04 ("d", br, 1 H), |
| | 3.80–3.70 (m, 1 H), |
| | 3.73 (s, 3 H), |
| | 3.39–3.36 ("dd", 1 H), |
| | 3.11–3.05 ("dd", 1 H), |
| | 3.05–2.92 (m, 2 H), |
| | 2.85–2.75 (m, 1 H), |
| | 2.23–2.13 (m, 1 H), |
| | 2.00–1.92 (m, 1 H), |
| | 1.46 (s, 9 H), |
| | 0.95 (d, J = 6.9 Hz, 3 H), |
| | 0.92 (d, J = 6.8 Hz, 3 H). |
| $^{13}$C-NMR (CDCl$_3$, 100 MHz): δ | 172.29 (s), |
| | 171.27 (s), |
| | 154.67 (s), |
| | 80.13 (s), |
| | 58.44 (d), |
| | 56.81 (d), |
| | 52.11 (q), |

| | |
|---|---|
| | 46.60 (br, t), |
| | 43.96 (t), |
| | 43.90 (br, t), |
| | 31.11 (d), |
| | 28.41 (q), |
| | 19.12 (q), |
| | 17.86 (q). |

EXAMPLE 4

Preparation of allyl 3-t-butylcarbamoylpiperazine-1-carboxylate 1.78 g (15.0 mmol) of thionyl chloride were added dropwise at 22° C. to 3.00 g (10.0 mmol) of the 1,4-diallyl ester of piperazine-1,2,4-tricarboxylic acid in 20 ml of methylene chloride. The mixture was subsequently stirred for a further 20 hours at 22° C. 2.92 g (40 mmol) of t-butylamine were added dropwise while cooling to this reaction solution over a period of 5 minutes. The suspension formed was maintained at 22° C. for a further 3 hours and then admixed with 50 ml of water and 50 ml of dichloromethylene. The phases were separated and the aqueous phase was extracted twice more with 30 ml each time of dichloromethylene. Drying of the combined organic phases over magnesium sulfate and evaporation gave 2.30 g (85%) of the title compound as a pale yellow oil. The crude product was purified by chromatography for complete characterization.

| | |
|---|---|
| $^1$H-NMR (DMSO-d$_6$, 400 MHz): δ | 7.30–7.20 (m, 1 H), |
| | 5.98–5.85 (m, 1 H), |
| | 5.28 ("d", 1 H), |
| | 5.19 ("d", 1 H), |
| | 4.58–4.48 (m, 2 H), |
| | 3.90–3.82 (m, 1 H), |
| | 3.70–3.62 (m, 1 H), |
| | 3.10–3.05 ("dd", 1 H), |
| | 2.90–2.80 (m, 3 H), |
| | 2.59–2.50 (m, 2 H), |
| | 1.25 (s, 9 H). |

We claim:

1. Process for preparing 2-piperazinecarboxamides in the form of the enantiomers or their enantiomer mixtures of formula:

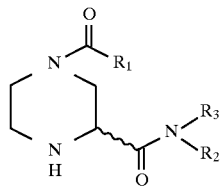

where $R_1$ is a) alkyl or alkyl substituted with phenyl or halogen, or b) —$OR_4$ where $R_4$ is alkyl, alkenyl, phenyl, naphthyl, alkyl substituted with phenyl or halogen, alkenyl substituted with phenyl or halogen, phenyl substituted with halogen or alkyl, or naphthyl substituted with halogen or alkyl, or c) —$NR_5R_6$, where $R_5$ is hydrogen, alkyl or alkyl substituted with phenyl or halogen, and $R_2$ and $R_3$ are identical or different and are hydrogen, alkyl, alkenyl, phenyl, naphthyl, alkyl substituted with phenyl or halogen, alkenyl substituted with phenyl or halogen, phenyl substituted with halogen or alkyl, naphthyl substituted with halogen or alkyl, or $R_3$ is hydrogen and $R_2$ is a residue of one of the essential L-α-amino acids selected from the group consisting of alanine, valine, leucine, isoleucine, proline, tryptophan, phenylalanine, methionine, glycine, serine, tyrosine, threonine, cysteine, asparagine, glutamine, aspartic acid, glutamic acid, lysine, arginine, histidine, and the ($C_1$–$C_4$)-alkyl esters thereof, comprising first converting a 2-piperazinecarboxylic acid of formula:

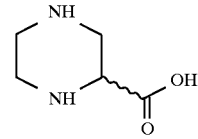

or a salt thereof, in the form of its enantiomers or its enantiomer mixtures, into an N-acyl derivative of formula:

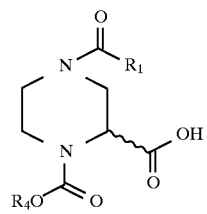

where $R_1$ and $R_4$ are as defined above, then cyclizing the N-acyl-derivative of the formula III in a second stage in the presence of a halogenating agent to form a piperazinecarboxylic anhydride of formula:

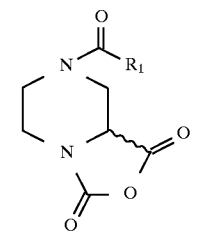

where $R_1$ is as defined above, and finally reacting the piperazinecarboxylic anhydride of formula IV with an amine of formula:

where $R_2$ and $R_3$ are as defined above, to give the end product of formula I.

2. Process according to claim 1, characterized in that $R_1$ is —$OR_4$.

3. Process according to claim 2, characterized in that the N-acyl derivative of the formula III is not isolated.

4. Process according to claim 3, characterized in that the halogenating agent used is thionyl chloride, a phosphorus halide, phosgene or a phosgene derivative.

5. Process according to claim 4, characterized in that thionyl chloride is used.

6. Process according to claim 5, characterized in that a N,N-disubstituted formamide is used in catalytic amounts of from 0.1 mol % to 30 mol %, based on the halogenating agent.

7. Process according to claim 6, characterize in that the reaction of the second stage is carries out at from 0° to 100° C.

8. Process according to claim 7, characterized in that the reaction with the amine of the formula V is carried out in the presence of an inert solvent or in aqueous alkaline solutions at a temperature of from −20° C. to the reflux temperature of the solvent.

9. Process according to claim 1, characterized in that the N-acyl derivative of the formula III is not isolated.

10. Process according to claim 1, characterized in that the halogenating agent used is thionyl chloride, a phosphorous halide, phosgene or a phosgene derivative.

11. Process according to claim 4, characterized in that a N,N-disubstituted formamide is used in catalytic amounts of from 0.1 mol percent to 30 mol percent, based on the halogenating agent.

12. Process according to claim 1, characterized in that the reaction of the second stage is carried out at from 0° to 100° C.

13. Process according to claim 1, characterized in that the reaction with the amine of the formula V is carried out in the presence of an inert solvent or in an aqueous alkaline solution at a temperature of from −20° C. to the reflux temperature of the solvent.

14. A piperazinecarboxylic anhydride of the formula:

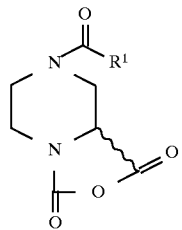

IV where $R_1$ is a) alkyl or alkyl substituted with phenyl or halogen, b) $OR_4$, where $R_4$ is alkyl, alkenyl, phenyl, naphthyl, alkyl substituted with phenyl or halogen, alkenyl substituted with phenyl or halogen, phenyl substituted with halogen or alkyl, or naphthyl substituted with halogen or alkyl, or c) —$NR_5R_6$, where $R_5$ is hydrogen or alkyl and $R_6$ is alkyl.

15. t-Butyl (R)-1,3-dioxotetrahydrooxazole[3,4-a]-piperazine-7-carboxylate.

16. t-Butyl (S)-1, 3-dioxotetrahydrooxazole[3,4-a]-piperazine-7-carboxylate.

17. Benzyl (R)-1,3-dioxotetrahydrooxazole[3,4-a]-piperazine-7-carboxylate.

18. Benzyl (S)-1,3-dioxotetrahydrooxazole[3,4-a]-piperazine-7-carboxylate.

19. Allyl (R)-1,3-dioxotetrahydrooxazole[3,4-a]-piperazine-7-carboxylate.

20. Allyl (S)-1,3-dioxotetrahydrooxazole[3,4-a]-piperazine-7-carboxylate.

* * * * *